United States Patent
Teshima et al.

(10) Patent No.: US 11,927,558 B2
(45) Date of Patent: Mar. 12, 2024

(54) MICROELECTRODE, METHOD OF MANUFACTURING SAME, AND INTEGRATED DEVICE

(71) Applicant: Nippon Telegraph and Telephone Corporation, Tokyo (JP)

(72) Inventors: Tetsuhiko Teshima, Musashino (JP); Yuko Ueno, Musashino (JP); Yui Ogawa, Musashino (JP); Yoshiaki Kashimura, Musashino (JP); Satoshi Sasaki, Musashino (JP); Shengnan Wang, Musashino (JP); Makoto Takamura, Musashino (JP); Hiroshi Nakashima, Musashino (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 651 days.

(21) Appl. No.: 17/255,341

(22) PCT Filed: Jul. 3, 2019

(86) PCT No.: PCT/JP2019/026472
§ 371 (c)(1),
(2) Date: Dec. 22, 2020

(87) PCT Pub. No.: WO2020/009152
PCT Pub. Date: Jan. 9, 2020

(65) Prior Publication Data
US 2021/0270764 A1    Sep. 2, 2021

(30) Foreign Application Priority Data
Jul. 4, 2018  (JP) .................... 2018-127882

(51) Int. Cl.
*G01N 27/30*   (2006.01)
*G01N 27/327*  (2006.01)

(52) U.S. Cl.
CPC ........ *G01N 27/327* (2013.01); *G01N 27/305* (2013.01)

(58) Field of Classification Search
CPC .................................................... G01N 27/30
See application file for complete search history.

(56) References Cited

U.S. PATENT DOCUMENTS

| | | | |
|---|---|---|---|
| 2003/0006669 A1* | 1/2003 | Pei ........ | H02N 11/006 310/309 |
| 2014/0212947 A1* | 7/2014 | Park ........ | C12Q 1/001 204/290.11 |

(Continued)

FOREIGN PATENT DOCUMENTS

JP    2014-226257    12/2014

OTHER PUBLICATIONS

Deng et al., "Self-folding graphene-polymer bilayers," Appl. Phys. Lett., 2015, 106:203108-1-203108-4.

(Continued)

*Primary Examiner* — Cachet I Proctor
(74) *Attorney, Agent, or Firm* — Fish & Richardson P.C.

(57) ABSTRACT

Provided is a microelectrode having a layered structure, including a layer containing a polymer compound having an aromatic ring (polymer compound layer) and a layer containing a conductive material (conductive layer), wherein a thickness of the polymer compound layer is 10 to 900 nm, a thickness of the conductive layer is 0.3 to 10 nm, and the microelectrode has a three-dimensional curved shape.

2 Claims, 9 Drawing Sheets

(56) References Cited

U.S. PATENT DOCUMENTS

2016/0007874 A1    1/2016  Ma et al.
2016/0100768 A1    4/2016  Someya et al.

OTHER PUBLICATIONS

Mohiuddin et al., "Uniaxial strain in graphene by Raman spectroscopy: G peak splitting, Grüneisen parameters, and sample orientation," Phys. Rev. B., 2009, 79:205433-1-205433-8.

Park et al., "Fabrication and utility of a transparent graphene neural electrode array for electrophysiology, in vivo imaging, and optogenetics," Nature Protocols, 2016, 11(11):2201-2222.

Park et al., "Graphene-based carbon-layered electrode array technology for neural imaging and optogenetic applications," Nat. Comm., 2014, 5:5258, 11 pages.

\* cited by examiner

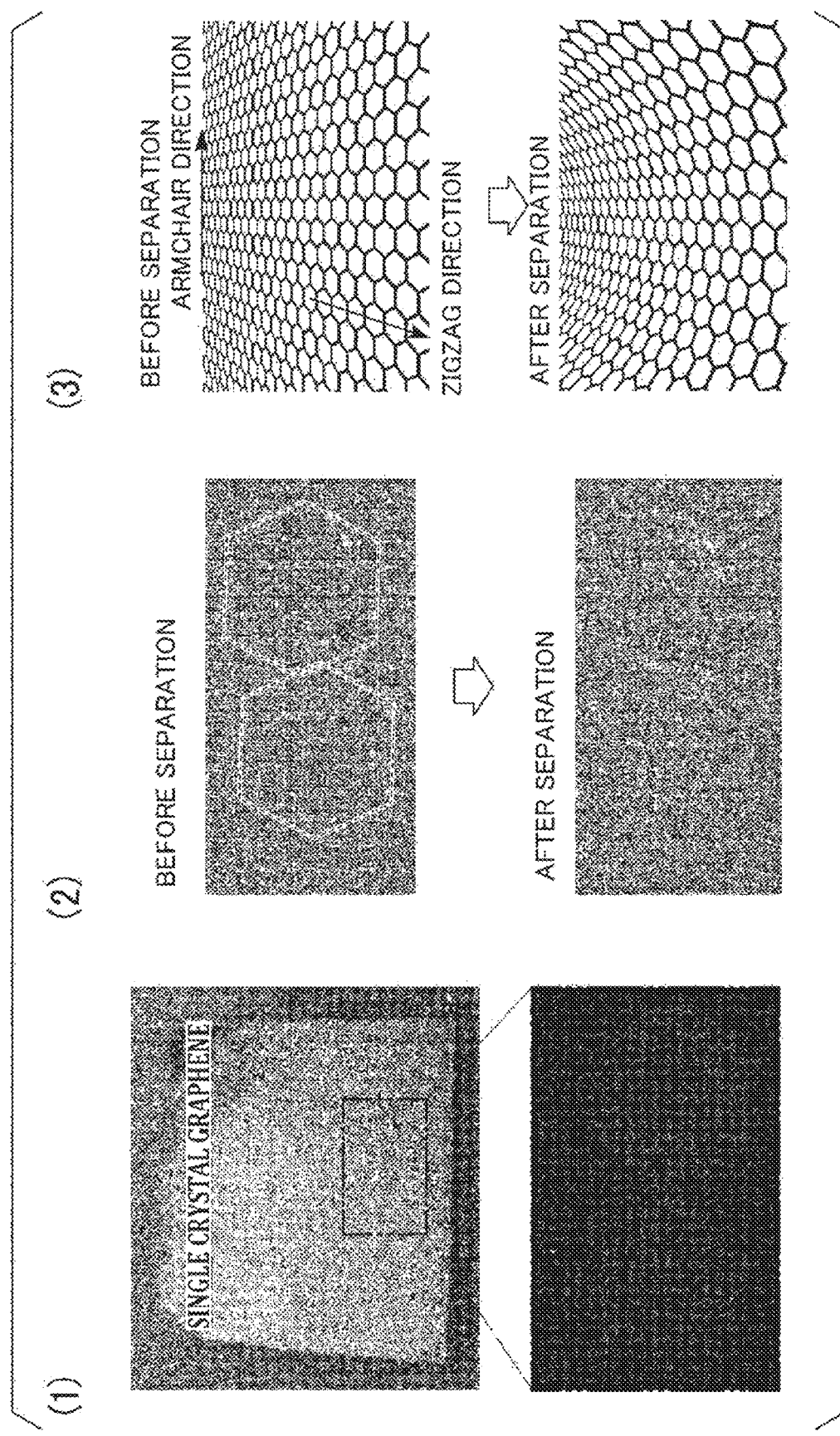

MICROELECTRODE, METHOD OF MANUFACTURING SAME, AND INTEGRATED DEVICE

CROSS-REFERENCE TO RELATED APPLICATIONS

This application is a National Stage application under 35 U.S.C. § 371 of International Application No. PCT/JP2019/026472, having an International Filing Date of Jul. 3, 2019, which claims priority to Japanese Application Serial No. 2018-127882, filed on Jul. 4, 2018. The disclosure of the prior application is considered part of the disclosure of this application, and is incorporated in its entirety into this application.

TECHNICAL FIELD

The present invention relates to a microelectrode, a method of producing the same, and an integrated device.

BACKGROUND ART

Recently, since materials such as indium and tin oxide are rare, and metal materials have low biocompatibility and high stiffness, it is absolutely essential to search for materials that can be used instead of metals in the application for electronic devices that especially have to be flexible and elastic. From the viewpoint of high electrical properties, thermal conductivity, mechanical strength, and mechanical flexibility, carbon materials such as graphene have been gaining attention as materials for flexible electronics and fuel cells. It is reported that graphene in particular has high biocompatibility and is useful also as an interface that realizes electrical connection with cells or living tissues.

Typically, graphene is a material having a two-dimensional plane structure. When practically applying graphene to devices, the degree of freedom in designing according to the applications increases if the shape can be changed in all dimensions ranging from one dimension to three dimensions. For example, materials derived from living bodies such as cells and living tissues have a three-dimensional shape, and thus, in order to function as an interface therefor, it is necessary to have a more minute three-dimensional structure.

Conventionally, in a state in which graphene is transferred to a flexible polymer substrate and then artificially buckled, its optical and electrical properties are measured (NPL 1). However, with such a method using buckling, it is difficult to produce a minute three-dimensional shape in a micrometer scale.

Thus, a technique has been gaining attention in which graphene is transferred to a thin film element that can be folded into a minute three-dimensional shape in a self-organized manner, and graphene with a minute three-dimensional form is produced using the thin film element as a power source (NPL 2).

Meanwhile, an electrode element produced by transferring graphene to polyparaxylene (parylene), which is a polymer material having many aromatic rings, also disclosed (NPL 3). In NPL 3, an electrode element is implanted on a living body, and electrical signals from living tissues are stably measured while the structure is maintained.

CITATION LIST

Non Patent Literature

[NPL 1] T. M. G. Mohiuddin, et. al., "Uniaxial strain in graphene by Raman spectroscopy: G peak splitting, Gruneisen parameters, and sample orientation", Phys. Rev. B, 2009, 79, 205433-1-8.
[NPL 2] T. Deng, et. al., "Self-folding graphene-polymer bilayers", Appl. Phys. Lett., 2015, 106, 203108-1-4.
[NPL 3] D. W. Park, et. al., "Graphene-based carbon-layered electrode array technology for neural imaging and optogenetic applications", Nat. Comm., 2014, 5, 5258-1-22.

SUMMARY OF THE INVENTION

Technical Problem

The technique described in NPL 2 is technically problematic in that graphene is likely to peel away or slip over the surface due to low adhesion between graphene and a thin film element, and breakage is likely to occur due to local stress concentration.

The technique described in NPL 3 uses parylene with high adhesion to graphene, and thus graphene is unlikely to peel away or slip over the surface, for example, but it is also problematic in that the degree of freedom in designing according to the applications is low because it has a two-dimensional plane structure.

In order to design graphene to a minute three-dimensional shape, it is desirable that a thin polymer film with high adhesion to graphene is used, and graphene itself applies a strain gradient to the thickness direction of the thin film, so that graphene itself functions as a power source for self-organized three-dimensional folding.

With the foregoing in view, it is an object of the present invention to provide a microelectrode having any three-dimensional curved shape in which coming off, slippage, breakage, and the like are suppressed, a method of producing the same, and an integrated device including the microelectrode.

Means for Solving the Problem

An aspect of the present invention is directed to a microelectrode having a layered structure, including a polymer compound layer which is a layer containing a polymer compound having an aromatic ring; and a conductive layer which is a layer containing a conductive material, wherein a thickness of the polymer compound layer is 10 to 900 nm; and a thickness of the conductive layer is 0.3 to 10 nm, and the microelectrode has a three-dimensional curved shape.

An aspect of the present invention is directed to the above-described microelectrode, wherein the conductive material is a conductive carbon material.

An aspect of the present invention is directed to the above-described microelectrode, wherein the polymer compound layer contains polyparaxylene or a derivative thereof.

An aspect of the present invention is directed to the above-described microelectrode, wherein the polymer compound layer and the conductive layer are arranged adjacent to each other.

An aspect of the present invention is directed to a method of producing a microelectrode with a three-dimensional curved shape, including steps of: (a) forming a layered member including a polymer compound layer which is a layer containing a polymer compound having an aromatic ring, wherein a thickness of the polymer compound layer is 10 to 900 nm; and a conductive layer which is a layer containing a conductive material, wherein a thickness of the conductive layer is 0.3 to 10 nm; and a step (b) of allowing the layered member to form a three-dimensional curved shape in a self-organized manner, using a strain gradient in a thickness direction of the layered member as a driving force.

An aspect of the present invention is directed to the above-described microelectrode producing method, further including a step of (c) patterning a part or all of the layers of the layered member into any shape, after the step (a) and before the step (b).

An aspect of the present invention is directed to an integrated device including the above-described microelectrode.

Effects of the Invention

According to the present invention, it is possible to provide a microelectrode having any three-dimensional curved shape in which coming off, slippage, breakage, and the like are suppressed, a method of producing the same, and an integrated device including the microelectrode.

BRIEF DESCRIPTION OF DRAWINGS

FIG. 5(1) shows a correlation between the radius of curvature of the tubular microelectrode and the thickness of a parylene layer (polymer compound layer). FIG. 5(2) shows a correlation between the radius of curvature of the tubular microelectrode and the number of graphene layers (conductive layer) transferred.

FIGS. 7(1) to 7(4) show the process for producing a tubular microelectrode that is an embodiment of the present invention. FIG. 7(5) shows I-V curves of the tubular microelectrode before self-folding (dry state, in water), and after self-folding (after addition of the EDTA solution, after replacement with pure water).

FIG. 8(1) shows a microelectrode with a spherical gripper structure. FIG. 8(2) shows a microelectrode with a pattern in which hexagons are arranged adjacent to each other to form an array. FIG. 8(3) shows a coil-like microelectrode.

FIG. 9 shows a state of control of the bending direction with the crystal orientation of graphene. FIG. 9(1) shows single crystal graphene produced in a millimeter size. FIG. 9(2) shows a state of bending when a layered member including a parylene layer and a single crystal graphene layer transferred to the parylene layer was separated from a substrate. FIG. 9(3) shows a conceptual diagram of bending of the layered member including a single crystal graphene layer.

DESCRIPTION OF EMBODIMENTS

Figure 1:
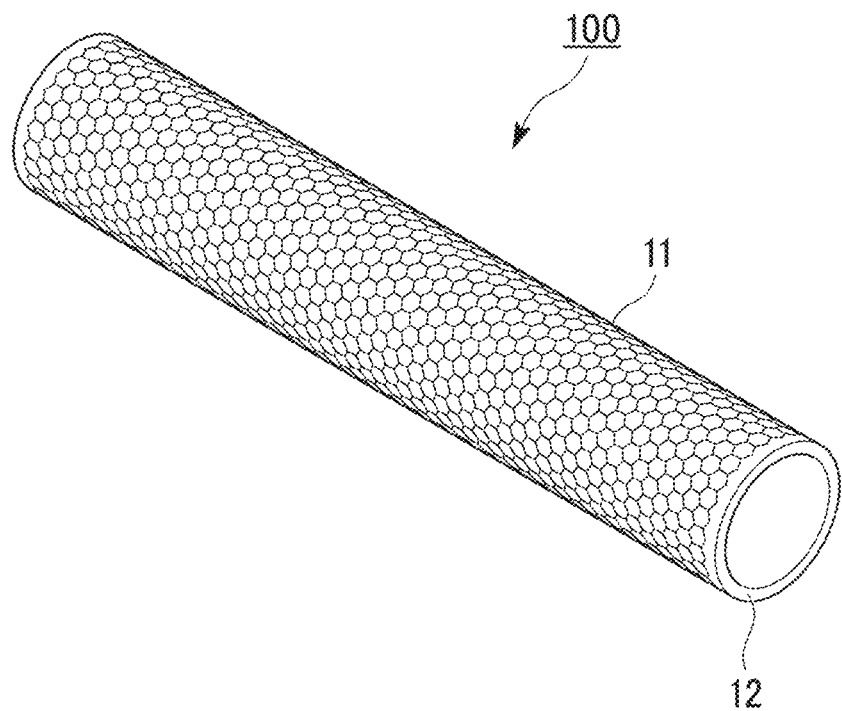
FIG. 1 is a perspective view of a microelectrode according to an embodiment of the present invention.

Hereinafter, an embodiment of the present invention will be described in detail with reference to the drawings in some cases. In the drawings, the same or corresponding constituent elements are denoted by the same reference numerals, and redundant descriptions thereof have been omitted. The proportions in the drawings may be exaggerated for the sake of description, and may not absolutely match the actual proportions.

<Microelectrode>

A microelectrode according to an embodiment of the present invention has a microelectrode having a layered structure, including a polymer compound layer which is a layer containing a polymer compound having an aromatic ring and a conductive layer which is a layer containing a conductive material, wherein a thickness of the polymer compound layer is 10 to 900 nm, a thickness of the conductive layer is 0.3 to 10 nm, and the microelectrode has a three-dimensional curved shape. Hereinafter, the microelectrode according to this embodiment will be described with reference to the drawings showing a preferred embodiment of the present invention.

FIG. 1 shows a microelectrode according to an embodiment of the present invention. In FIG. 1, 100 denotes a microelectrode, 11 denotes a conductive layer, and 12 denotes a polymer compound layer.

As shown in FIG. 1, the microelectrode 100 has a structure in which the polymer compound layer 12 is stacked on the conductive layer 11. That is to say, the conductive layer 11 is arranged on the outer side, and the polymer compound layer 12 is arranged on the inner side.

In the microelectrode 100 shown in FIG. 1, the conductive layer 11 and the polymer compound layer 12 are arranged adjacent to each other. In the microelectrode of this embodiment, the conductive layer 11 and the polymer compound layer 12 do not absolutely have to be adjacent to each other, but it is preferable that the conductive layer 11 and the polymer compound layer 12 are adjacent to each other at least in a portion in which a three-dimensional curved shape is to be formed. It is more preferable that the conductive layer 11 and the polymer compound layer 12 are in close contact with each other in a portion in which a three-dimensional curved shape is to be formed.

The microelectrode of this embodiment has a three-dimensional curved shape. "Having a three-dimensional curved shape" means a state in which at least part of the structure of the microelectrode has a shape that is curved in three dimensions. For example, in the example in FIG. 1, the microelectrode 100 has a shape in which the entire structure is curved into a tubular shape. The tubular microelectrode as shown in FIG. 1 is a preferred example of the microelectrode of this embodiment. However, the three-dimensional curved shape that the microelectrode of this embodiment may have is not limited to the example in FIG. 1, and, for example, it is also possible that part of the structure has a shape that is curved in three dimensions (see FIG. 7(4), for example). Alternatively, it may be a spherical gripper structure, or may be a helical structure (see FIG. 8, for example). Further examples thereof include various three-dimensional curved shapes such as a living tissue-like structure.

It is possible to design the microelectrode of this embodiment as those with various three-dimensional curved shapes, by changing the thicknesses and the shapes of the conductive layer and the polymer compound layer.

(Conductive Layer)

The conductive layer 11 is a layer containing a conductive material. There is no particular limitation on the conductive material that is used in the conductive layer 11 as long as it is conductive, but the material is preferably a nanomaterial that can be processed into a thin film shape (a material in which at least one dimension thereof is 100 nm or less). Furthermore, the material is preferably a material that does not induce a significant change in the volume when immersed in a solution. In the case in which the microelectrode 100 is applied to a living body, a living tissue, or the like, the conductive material is preferably a biocompatible material.

Furthermore, the conductive material is preferably a material having a n-n interaction with the polymer compound contained in the polymer compound layer 12. Those practicing the invention can increase the adhesion between the conductive layer 11 and the polymer compound layer 12, by selecting these materials.

Examples of the conductive material include conductive carbon materials such as graphene and carbon nanotube, and planar material such as molybdenum disulfide. Of these, the conductive material preferably contains a conductive carbon material, and more preferably contains graphene. The number of types of conductive materials contained in the conductive layer 11 may be one, or two or more, but is preferably one. In a preferred embodiment, the conductive layer 11 may be made of graphene, or made of buckypaper obtained by processing a carbon nanotube into a sheet form.

The conductive layer 11 may be made of a single-layered or multi-layered conductive material. In the case in which the conductive layer 11 is made of a multi-layered conductive material, there is no particular limitation on the number of layers of the conductive material, but it may be, for example, 2 to 30 layers, 2 to 20 layers, 2 to 10 layers, 2 to 5 layers, or the like. The conductive layer 11 is preferably made of a conductive carbon material with 1 to 30 layers, and more preferably made of a conductive carbon material with 1 to 4 layers in order to maintain the transparency of the three-dimensional shape. The conductive layer 11 is more preferably made of graphene with 1 to 30 layers, and particularly preferably made of graphene with 1 to 4 layers in order to maintain the transparency of the three-dimensional shape. In the case in which the conductive layer 11 is made of graphene, it may be either polycrystalline graphene or single crystal graphene, but it is preferably single crystal graphene from the viewpoint of controlling the direction of the curved shape.

The thickness of the conductive layer 11 is 0.3 to 10 nm. If the conductive layer 11 is made of a multi-layered conductive material, the total thickness of the plurality of layers is the thickness of the conductive layer 11. Those practicing the invention can allow the layered member constituting the microelectrode 100 to form a three-dimensional curved shape in a self-organized manner, by setting the thickness of the conductive layer 11 to the above-described range and setting the thickness of the polymer compound layer 12 to a later-described predetermined range. From the viewpoint of forming a stable three-dimensional curved shape, the thickness of the conductive layer 11 is preferably 0.3 to 7 nm, more preferably 0.3 to 5 nm, and even more preferably 0.3 to 1.2 nm. Those practicing the invention can obtain a microelectrode 100 having any three-dimensional curved shape, by controlling the ratio of the thickness of the conductive layer 11 with respect to the thickness of the polymer compound layer 12 within the above-described range. For example, it is possible to reduce the radius of curvature of the three-dimensional curved shape, by increasing the thickness of the conductive layer 11 with respect to the thickness of the polymer compound layer 12.

(Polymer Compound Layer)

The polymer compound layer 12 is a layer containing a polymer compound having an aromatic ring. The polymer compound that is used in the polymer compound layer 12 is preferably a compound having many aromatic rings in molecules, and having a n-n interaction with the conductive material contained in the conductive layer 11. With such a polymer compound, the adhesion of the polymer compound layer 12 to the conductive layer 11 increases. Furthermore, In the case in which the microelectrode 100 is applied to a living body, a living tissue, or the like, it is preferable to use a polymer compound that has high transparency and is not toxic to cells. Examples of such a polymer compound include polyparaxylene and a derivative thereof. Examples of the derivative of polyparaxylene include polymers such as halogenated paraxylene (chloroparaxylene, fluoroparaxylene, etc.). Of these, the polymer compound is more preferably polyparaxylene.

The number of types of polymer compounds contained in the polymer compound layer 12 may be one, or two or more, but is preferably one.

The thickness of the polymer compound layer 12 is 10 to 900 nm. If the polymer compound layer 12 is made of a multi-layered thin film, the total thickness of the plurality of layers of thin film is the thickness of the polymer compound layer 12. Those practicing the invention can allow the layered member constituting the microelectrode 100 to form a three-dimensional curved shape in a self-organized manner, by setting the thickness of the polymer compound layer 12 to the above-described range and setting the thickness of the conductive layer 11 to the above-described predetermined range. From the viewpoint of forming a stable three-dimensional curved shape, the thickness of the polymer compound layer 12 is preferably 40 to 400 nm, and more preferably 50 to 250 nm. Those practicing the invention can obtain a microelectrode 100 having any three-dimensional curved shape, by controlling the ratio of the thickness of the polymer compound layer 12 with respect to the thickness of the conductive layer 11 within the above-described range. For example, those practicing the invention can increase the radius of curvature of the three-dimensional curved shape, by increasing the thickness of the polymer compound layer 12 with respect to the thickness of the conductive layer 11.

There is no particular limitation on the thickness ratio between the conductive layer 11 and the polymer compound layer 12 (the thickness of the conductive layer 11/the thickness of the polymer compound layer 12) as long as it is from 1/3000 to 1/1, but it is preferably from 1/1200 to 1/4. Those practicing the invention can form a stable three-dimensional curved shape, by setting the thickness ratio between the conductive layer 11 and the polymer compound layer 12 to the above-described range.

(Other Constituent Elements)

The microelectrode of this embodiment may have other constituent elements in addition to the conductive layer 11 and the polymer compound layer 12 described above, within the range not impairing the effects of the present invention.

Examples of the other constituent elements include a metal layer.

—Metal Layer

The metal layer is a layer containing a metal element. When evaluating the electrical properties of the microelectrode, in particular when allowing the current to flow at an end thereof using a probe, if a single-layered graphene film or the like is used as the conductive layer 11, an end of the probe cannot be directly put into close contact with the conductive layer 11, whereas, if the microelectrode has a metal layer with a mechanical strength that can prevent the layer from coming off due to the probe, the shape of the microelectrode can be maintained. There is no particular limitation on the metal element that is contained in the metal layer as long as it is an element that is commonly used in metal electrodes, but examples thereof include noble metals such as gold, silver, platinum, palladium, rhodium, iridium, ruthenium, and iridium. There is no particular limitation on the thickness of the metal layer, but it is preferably, for example, 10 nm to 100 μm. If the microelectrode of this embodiment includes a metal layer, the metal layer is preferably arranged at a portion not having a three-dimensional curved shape.

In the microelectrode 100, the thickness of the entire layered structure of a portion having a three-dimensional curved shape (the total thickness of the conductive layer 11, the polymer compound layer 12, and the metal layer and other layers as necessary) is preferably approximately 10 to 500 nm, in order not to hinder bending in a later-described production step.

In a preferable specific examples of the microelectrode 100, the conductive layer is made of graphene, the polymer compound layer is made of polyparaxylene or a derivative thereof, and the conductive layer and the polymer compound layer are adjacent to each other. Since graphene and polyparaxylene or a derivative thereof have particularly high adhesion to each other, this configuration can suppress occurrence of coming off, slippage, breakage, and the like even in a three-dimensional curved shape portion.

In this embodiment, those practicing the invention can form the microelectrode into a three-dimensional curved shape, by setting the thicknesses of the polymer compound layer containing a polymer compound having an aromatic ring and the conductive layer respectively to the predetermined thicknesses. Furthermore, those practicing the invention can increase the adhesion to the conductive layer and suppress occurrence of coming off, slippage, breakage, and the like, by using a polymer compound having an aromatic ring for the polymer compound layer. Moreover, those practicing the invention can produce a microelectrode with any three-dimensional curved shape, by designing the thickness, the two-dimensional pattern, and the like, as necessary. Furthermore, if graphene is used as the conductive material, it is possible to define the curve direction to any direction, by controlling the crystal orientation of graphene.

The microelectrode of this embodiment can be re-arranged to any location through an operation with a micromanipulator, and it is possible to perform evaluation of electrical properties, integration into a device, assembly of a circuit, and the like.

In particular, if graphene is used as the conductive material and polyparaxylene or a derivative thereof is used as the polymer compound, since graphene, and polyparaxylene and derivatives thereof are materials with high durability, they are unlikely to change their shapes or to be strained even when they are immersed in a liquid over a long period of time or the liquid change in the temperature s. Furthermore, since graphene, and polyparaxylene and derivatives thereof have high transparency, they do not block an optical path during observation using a microscope, and can be used microscopes of types such as the upright type or the inverted type. Moreover, it is also possible to realize high-precision observation through observation using a super-resolution microscope. In addition, it is also possible to perform handling such as collecting or moving through a pipetting operation, and, furthermore, to form a plurality of microelectrodes into an organized structure using a glass capillary.

Furthermore, it is possible to realize the application as an electrode interface and the like to cells and tissues, by using a biocompatible material as the conductive material and the polymer compound. Graphene, and polyparaxylene and derivatives thereof are preferable as the biocompatible material.

<Microelectrode Producing Method>

The method of producing a microelectrode with a three-dimensional curved shape according to an embodiment of the present invention has the following two steps. The first step is a step (a) of forming a layered member including a layer containing a polymer compound having an aromatic ring (polymer compound layer) with a thickness of 10 to 900 nm, and a layer containing a conductive material (conductive layer) with a thickness of 0.3 to 10 nm. The second step is a step (b) of allowing the layered member to form a three-dimensional curved shape in a self-organized manner, using, as a driving force, a strain gradient in a thickness direction of the layered member. Hereinafter, the microelectrode producing method of the present invention will be described with reference to the drawings showing a preferred embodiment of the present invention.

Figure 2:
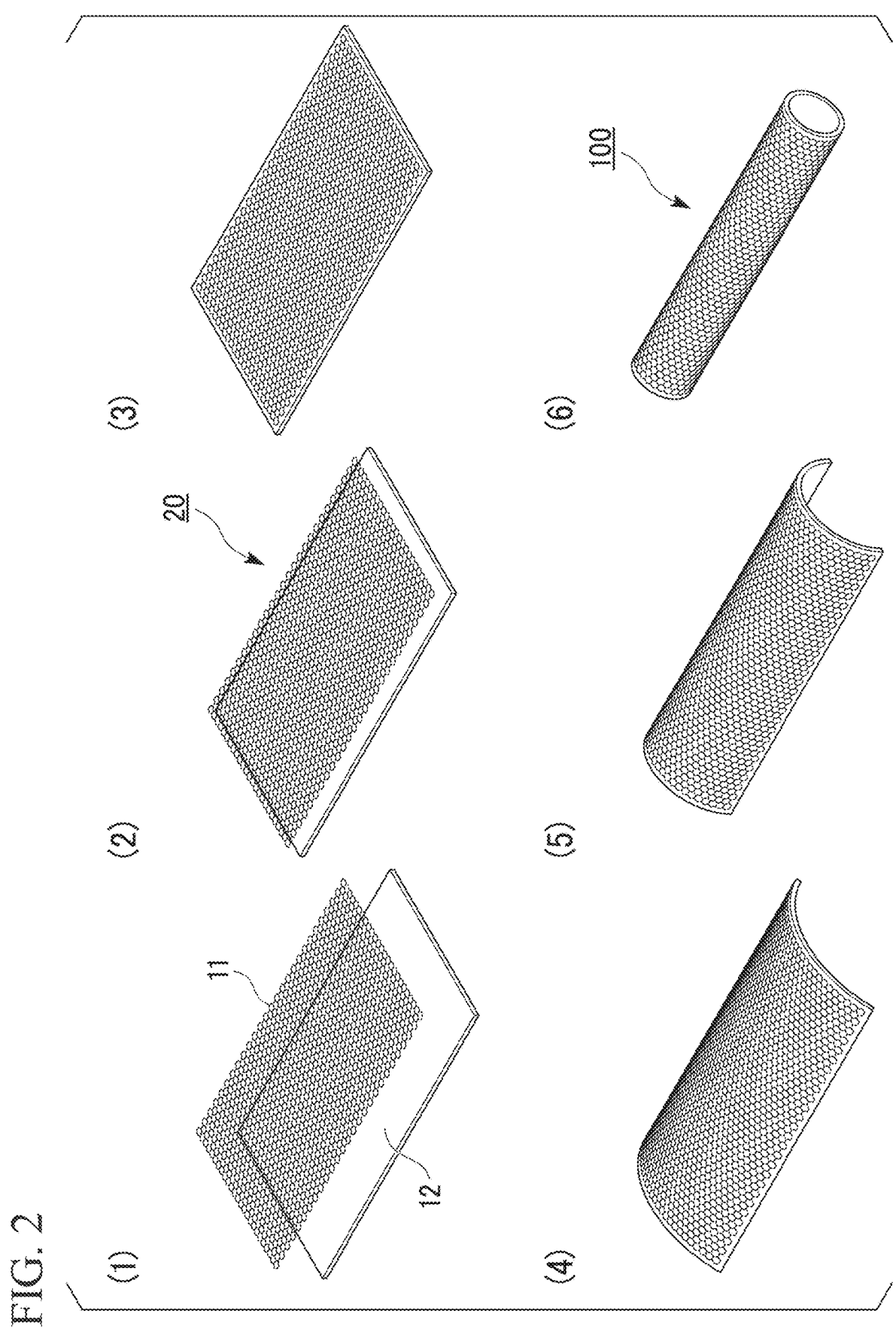
FIG. 2 is a schematic view of a microelectrode producing method according to an embodiment of the present invention.

FIG. 2 is a view showing the outline of the producing method microelectrode according to an embodiment of the present invention.

First, a layered member 20 including the conductive layer 11 and the polymer compound layer 12 is formed (FIGS. 2(1) and 2(2): step (a)). In the example in FIGS. 1(1) and 1(2), the conductive layer 11 and the polymer compound layer 12 are each formed (FIG. 1(1)), and the conductive layer 11 is transferred to the polymer compound layer 12 (FIG. 1(2)), so that the layered member 20 is formed.

Then, the layered member 20 is allowed to form a three-dimensional curved shape in a self-organized manner, using, as a driving force, the strain gradient in the thickness direction of the layered member 20 (FIGS. 1(3) to 1(6): step (b)). In the example in FIGS. 1(3) to 1(6), the conductive layer 11 and the polymer compound layer 12 are put into close contact and connected to each other (FIG. 2(3)), so that stress distribution appears in the thickness direction of the layered member 20, and a strain gradient in the in-plane direction is formed (FIG. 2(4)). The conductive layer 11 and the polymer compound layer 12 that have been connected to each other are bent using this strain gradient as a driving force (FIG. 2(5)), and thus a three-dimensional curved shape are obtained in a self-organized manner (FIG. 2(6)).

Hereinafter, the steps of the microelectrode producing method according to this embodiment will be described.

[Step (a)]

The step (a) is a step (a) of forming a layered member including a polymer compound layer with a thickness of 10 to 900 nm and a conductive layer with a thickness of 0.3 to 10 nm.

Figure 3:
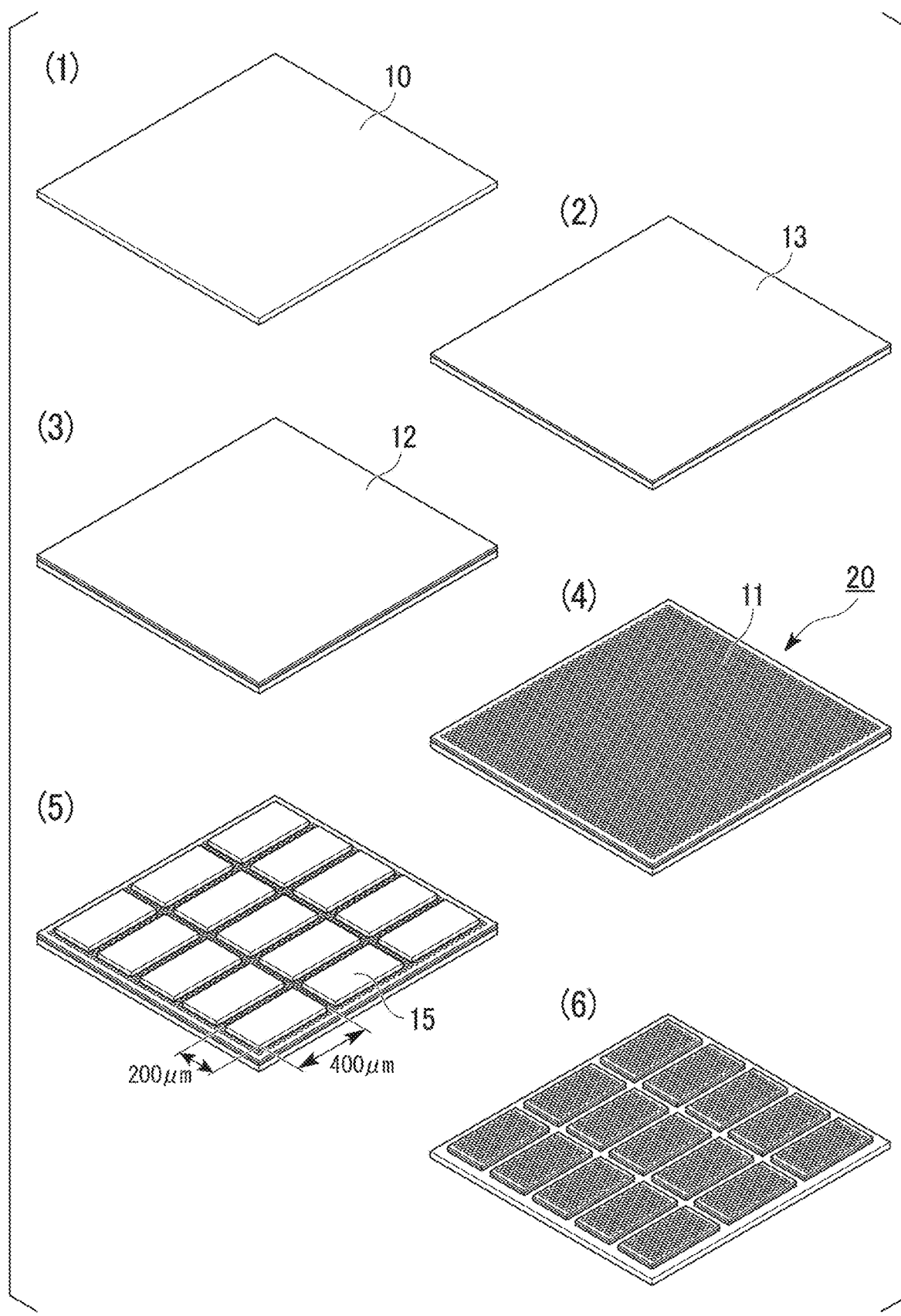
FIG. 3 is an example of the processing flow for forming a layered member 20.

FIGS. 3(1) to 3(4) are views showing a specific example of the method for forming the layered member 20 including the polymer compound layer 12 and the conductive layer 11.

In the example in FIGS. 3(1) to 3(4), a sacrificial layer 13 is formed (FIG. 3(2)) on a substrate 10 (FIG. 3(1)), and the polymer compound layer 12 (FIG. 3(3)) and the conductive layer 11 (FIG. 3(4)) are formed thereon, so that the layered member 20 is formed.

(Substrate)

The substrate 10 is used for the sake of formation of the layered member 20, and there is no particular limitation on its material. The material of the substrate 10 is preferably a material with high surface flatness. Furthermore, if observation is performed using a fluorescence microscope or the like in a state in which a cell is enclosed by the microelectrode produced according to the method of this embodiment that has been held on the substrate, it is preferably a material that does not disturb the observation of the fluorescence intensity of the cell using the fluorescence microscope and that has a wavelength absorption band as optical properties not overlapping that of the conductive layer 11.

Examples of the material of the substrate 10 include silicon, soda glass, quartz, magnesium oxide, and sapphire.

There is no particular limitation on the thickness of the substrate 10, but it is preferably approximately 50 to 200 μm.

Specific examples of the substrate 10 include a glass substrate with a thickness of approximately 100 μm.

(Sacrificial Layer)

The sacrificial layer 13 has a function as a temporary adhesion layer for separating the layered member 20 including the conductive layer 11 and the polymer compound layer 12 from the substrate 10. There is no particular limitation on the material for forming the sacrificial layer 13 as long as it is a material that melts in response to a stimulation from the outside such as a chemical material, a change in the temperature, irradiation with light, or the like. Examples of the sacrificial layer 13 include a calcium alginate gel, which is a type of physical gel. The calcium alginate gel melts through transition of the calcium alginate gel from gel to sol in response to the addition of a chelating agent such as sodium citrate or ethylene diamine tetra acetic acid (EDTA), an enzyme called arginase, or the like. Since the sacrificial layer 13 melts in response to a stimulation from the outside, those practicing the invention can separate the layered member 20 from the substrate 10 by melting the sacrificial layer 13 in a later-described step (b), thereby allowing the layered member 20 to form a three-dimensional curved shape in a self-organized manner. Since the chelating agent such as sodium citrate or ethylene diamine tetra acetic acid (EDTA) is not toxic to biological samples such as cell, a target cell can be enclosed by suspending the cell immediately before melting of the sacrificial layer 13.

The material of the sacrificial layer 13 may be any other materials regardless of the type such as synthetic polymers or biopolymers, as long as they are materials that melt in response to a stimulation from the outside. Preferred examples thereof include a thin metal film that can be melted by an etchant, poly(N-isopropylacrylamide) whose gel-sol transition can be induced by a change in the temperature, photoresists whose gel-sol transition can be induced by irradiation with ultraviolet light, and the like.

There is no particular limitation on the thickness of the sacrificial layer 13. The thickness of the sacrificial layer 13 may be, for example, 20 to 1000 nm, from the viewpoint of realizing quick melting.

There is no particular limitation on the method for forming the sacrificial layer 13 on the substrate 10, and methods commonly used to form a thin film can be selected as appropriate according to the material of the sacrificial layer 13. Examples of the method for forming the sacrificial layer 13 include chemical vapor deposition (CVD), spin coating, inkjet printing, vapor deposition, and electrospraying.

(Conductive Layer, Polymer Compound Layer)

The conductive layer 11 and the polymer compound layer 12 as are described in "<Microelectrode>" above.

In the example in FIGS. 3(3) and 3(4), the polymer compound layer 12 is formed on the sacrificial layer 13, and then the conductive layer 11 is formed on the polymer compound layer 12, but the forming order may be opposite.

That is to say, it is also possible that the conductive layer 11 is formed on the sacrificial layer 13, and then the polymer compound layer 12 is formed on the conductive layer 11.

The thickness of the conductive layer 11 formed in this step is 0.3 to 10 nm, and the thickness of the polymer compound layer 12 is 10 to 900 nm. Those practicing the invention can form a strain gradient in the thickness direction of the layered member 20, by setting the thicknesses of the conductive layer 11 and the polymer compound layer 12 to the above-described range. If the thickness of the conductive layer 11 is larger within the above-described range, the radius of curvature of the three-dimensional curved shape formed in a later-described step (b) is smaller. On the other hand, if the thickness of the polymer compound layer 12 is larger within the above-described range, the radius of curvature of the three-dimensional curved shape formed in a later-described step (b) is larger.

There is no particular limitation on the method for forming the polymer compound layer 12, and examples thereof include CVD, spin coating, inkjet printing, vapor deposition, and electrospraying. For example, if the polymer compound layer 12 is made of polyparaxylene or a derivative thereof, it is possible to form the polymer compound layer 12 by causing a dimer of the paraxylene or derivative thereof to grow through CVD.

There is no particular limitation on the method for forming the conductive layer 11, and examples thereof include transfer using a water surface, chemical vapor deposition (CVD), spin coating, inkjet printing, thermal vapor deposition, and electrospraying. For example, if the conductive layer 11 is made of graphene, those practicing the invention can form the conductive layer 11, by forming a single-layered graphene film through CVD on the surface of a metal film such as a copper foil, melting the metal film, repeating washing on the water surface, and transferring the single-layered graphene film to the surface of the polymer compound layer 12 or the sacrificial layer 13. Moreover, it is possible to form the conductive layer 11 made of multi-layered graphene, by repeating the above-described processing.

(Other Constituent Elements)

The layered member 20 formed in this step may include other constituent elements in addition to the conductive layer 11 and the polymer compound layer 12 described above. There is no particular limitation on the other constituent elements, and they can be selected as appropriate according to the purpose. Examples of the other constituent elements included in the layered member 20 include an additional layer other than the conductive layer 11 and the polymer compound layer 12. The thickness, the forming method, and the like of the additional layer can be selected as appropriate according to the material for forming the layer. For example, the layered member 20 may include a metal layer as the additional layer. If the layered member 20 includes a metal layer, the thickness of the metal layer may be, for example, 10 nm to 100 μm. The metal layer may be provided adjacent to the conductive layer 11, and it is possible that, after the conductive layer 11 is formed on the sacrificial layer 13, the metal layer is formed on the conductive layer 11. Alternatively, it is also possible that, after the polymer compound layer 12 is formed on the sacrificial layer 13, the metal layer is formed on the polymer compound layer 12, and the conductive layer 11 is formed on the metal layer. In this case, it is preferable that the metal layer is not formed in a portion in which a three-dimensional curved shape is to be formed in a later-described step (b).

There is no particular limitation on the method for forming the metal layer, and examples thereof include vapor deposition, sputtering, and direct application (e.g., direct application of silver paste).

[Step (b)]

The step (b) is a step of allowing the layered member to form a three-dimensional curved shape in a self-organized manner, using, as a driving force, a strain gradient in a thickness direction of the layered member.

It is possible to form a strain gradient in the thickness direction of the layered member, by putting the conductive layer 11 and the polymer compound layer 12 respectively having predetermined thicknesses into close contact and connecting them to each other. In the example in FIG. 3, the polymer compound layer 12 and the conductive layer 11 are formed on the sacrificial layer 13, so that a strain gradient is formed in the thickness direction of the layered member 20. When the sacrificial layer 13 melts, the layered member 20 is allowed to form a three-dimensional curved shape in a self-organized manner, using the strain gradient as driving force.

The sacrificial layer 13 can be melted as appropriate according to the material of the sacrificial layer 13. For example, if the sacrificial layer 13 is made of a calcium alginate gel, it is possible to melt the sacrificial layer 13 by adding a chelating agent such as sodium citrate or ethylene diamine tetra acetic acid (EDTA), an enzyme called arginase, or the like. Furthermore, if the sacrificial layer 13 is a thin metal film that can be melted by an etchant, it can be melted by an etchant, if it is poly(N-isopropylacrylamide) whose gel-sol transition can be induced by a change in the temperature, it can be melted by a change in the temperature, and, if it is a photoresist whose gel-sol transition can be induced by irradiation with ultraviolet light, it can be melted by irradiation with ultraviolet light.

In an embodiment, the producing method according to this embodiment may also have the following steps. The steps are a step of forming the sacrificial layer 13 on the substrate 10, a step of forming the layered member 20 including the polymer compound layer 12 and the conductive layer 11 on the sacrificial layer 13, and a step of melting the sacrificial layer 13, and allowing the layered member 20 to form a three-dimensional curved shape in a self-organized manner by using, as a driving force, the strain gradient in the thickness direction of the layered member 20. Furthermore, it is also possible that the step of forming the layered member 20 is a step of forming the polymer compound layer 12 on the sacrificial layer 13 and forming the conductive layer 11 on the polymer compound layer 12, or a step of forming the conductive layer 11 on the sacrificial layer 13 and forming the polymer compound layer 12 on the conductive layer 11.

[Other Steps]

The producing method according to this embodiment may include other steps other than the steps (a) and (b). There is no particular limitation on the other steps, but examples thereof include a step (c) of patterning part or all of the layers of the layered member into any shape, after the step (a) and before the step (b).

There is no particular limitation on the patterning method. Examples thereof include microfabrication techniques such as photolithography, electron beam lithography, and dry etching.

There is no particular limitation on the pattern shape, and examples thereof include any pattern shape with various two-dimensional shapes and sizes. For example, in the example in FIG. 3(5), a pattern with rectangles each in which the vertical and horizontal lines are respectively 400 μm and 200 μm, but the shapes and sizes of the pattern are not limited to this. It is preferable that the size of the pattern is larger than 10 μm.

Figure 8:
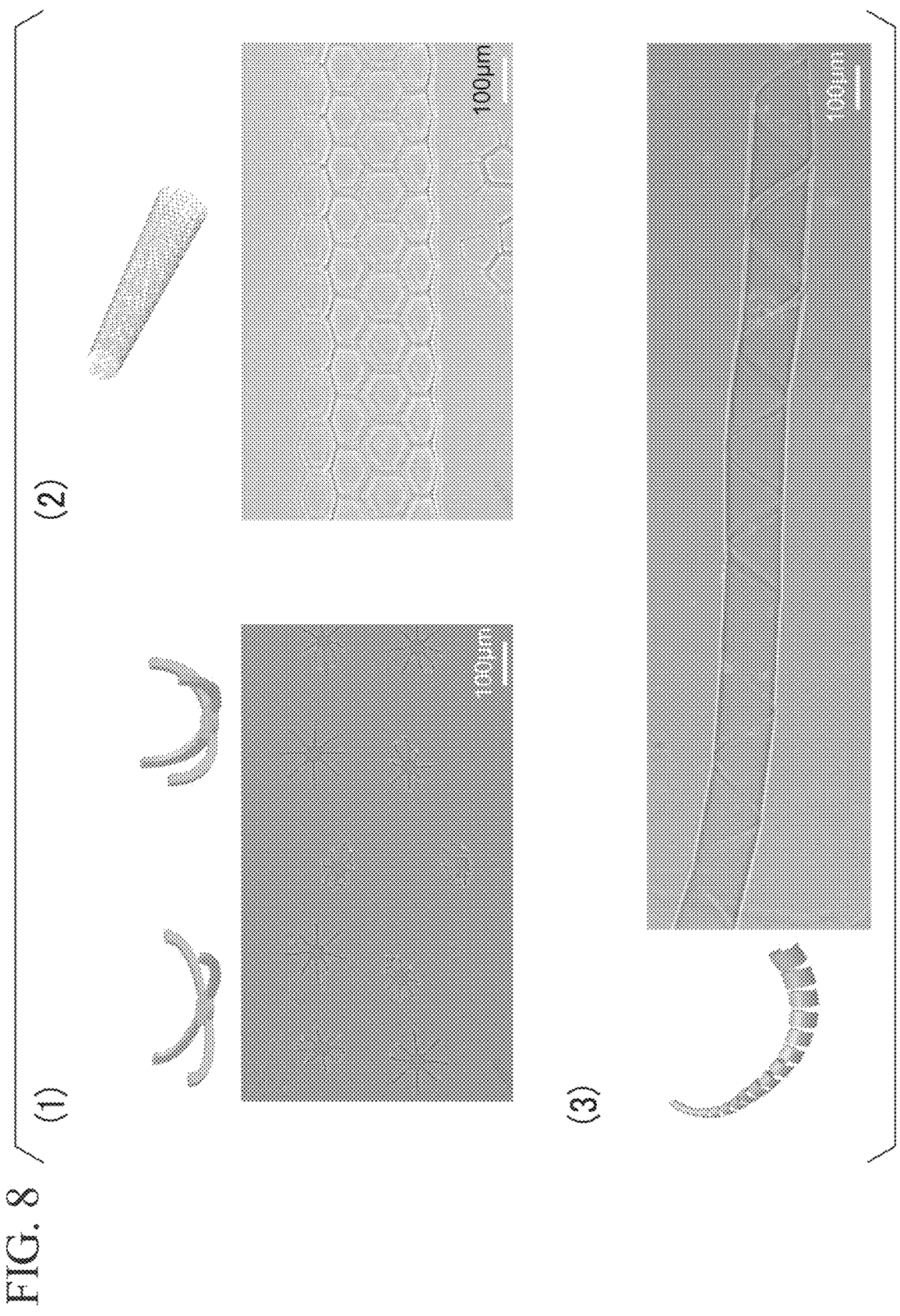
FIG. 8 shows microelectrodes with various three-dimensional curved shapes.

Those practicing the invention can obtain a microelectrode with a tubular shape by setting the pattern shape to a rectangular shape, and obtain a microelectrode with a spherical gripper structure by setting the pattern shape to a radial shape (see FIG. 8(1)). It is possible to obtain a microelectrode with a tubular shape structure that is larger, hollow, and has higher material permeability, by setting the pattern shape to a two-dimensional pattern in which hexagons are arranged adjacent to each other to form an array (see FIG. 8(2)). Also, if the pattern shape is set to a two-dimensional pattern structure of parallelograms in which two sides of each rectangle are inclined, it is possible to obtain a microelectrode with a coil-like structure that is wound along the inclined sides (see FIG. 8(3)). This coil structure can be applied as an electrode element whose structure can be flexibly changed in the major axis direction, and that is unlikely to break and is elastic.

With the microelectrode producing method according to this embodiment, those practicing the invention forms a strain gradient in the thickness direction of the layered member, by forming a layered member including the conductive layer and the polymer compound layer respectively having predetermined thicknesses, and allows the layered member to form a three-dimensional curved shape in a self-organized manner. In particular, those practicing the invention can suppress coming off, slippage, breakage, and the like caused by a change of the structure into a three-dimensional shape, by using materials having high adhesion to each other as the conductive layer and the polymer compound layer. Furthermore, those practicing the invention can obtain a microelectrode with any three-dimensional shape and size, by designing the shape of the layered member into the any shape and size.

<Integrated Device>

The integrated device according to an embodiment of the present invention is an integrated device including a microelectrode of the foregoing embodiment.

Since the microelectrode of the foregoing embodiment can have any minute shape, if electrode elements are folded in a three-dimensional manner and integrated, an integrated device can be produced. For example, if the microelectrodes of the foregoing embodiment are manipulated and placed using a manipulator or the like, the microelectrodes can be formed into an organized structure or into a circuit.

It is possible to apply the integrated device of this embodiment as, for example, an electrode interface to cells and tissues, by using a biocompatible material in the microelectrode.

In the description above, embodiments of the present invention have been described in detail with reference to the drawings, but specific configuration thereof is not limited to those of the embodiments, and the invention encompasses other designs and the like within the range not departing the gist thereof.

EXAMPLES

Hereinafter, the present invention will be described in more detail by way of specific examples. Note that the present invention is not limited to the examples described below.

[Example 1] Production Example of Layered Member

A microelectrode with a three-dimensional curved shape was produced produce according to the processing in FIGS. 3(1) to 3(6).

As the substrate 10 shown in FIG. 3(1), a glass substrate was used. A sodium alginate solution was spin-coated on the glass substrate, and then the resultant was immersed in 100 mM of calcium chloride solution, so that a sacrificial layer 13 made of calcium alginate gel was formed (FIG. 3(2)). The thickness of the sacrificial layer 13 can be controlled by changing the concentration of the sodium alginate solution and the speed of the spin coating. In this example, a 40-nm gel layer was formed through spin coating using 2 wt % of sodium alginate solution at 3000 rpm.

Next, a paraxylene dimer was caused to grow through CVD on the surface of the sacrificial layer 13, so that a polymer compound layer 12 made of polyparaxylene (parylene) was formed (FIG. 3(3)). The thickness of the polymer compound layer 12 can be controlled with the weight of paraxylene dimer that was used as a raw material of CVD growth. In this example, 50 mg of paraxylene dimer was caused to grow through CVD on the substrate 10, so that a 50-nm polymer compound layer 12 was formed.

Next, the conductive layer 11 was transferred to the surface of the polymer compound layer 12. In this example, as the conductive layer 11, single-layered graphene produced through CVD on the surface of a copper foil was used. The copper foil was melted by a ferric chloride solution, and, after washing was repeated on the water surface, the single-layered graphene (the conductive layer 11) was transferred to the surface of the polymer compound layer 12 (FIG. 3(4)). Those practicing the invention can stack multi-layered graphene on the surface of the polymer compound layer 12, by repeating this processing.

Next, a photoresist was spin-coated on the conductive layer 11, and then the resultant was irradiated with ultraviolet light through a photomask with any shape, so that a resist layer 15 was produced (FIG. 3(5)). Subsequently, etching was performed with oxygen plasma (FIG. 3(6)). The etching was performed until the sacrificial layer 13 formed on the substrate 10 was reached. Lastly, the resist layer 15 was removed with acetone, so that the conductive layer 11 was exposed as the upper face.

[Example 2] Production of Microelectrode

An EDTA solution, which is a chelating agent, was added to the layered member on the substrate 10 produced in [Example 1], so that the sacrificial layer 13 was melted. After the EDTA solution was added, the sacrificial layer 13 was slowly removed from the peripheral portion, and the reaction gradually progressed to the center portion. Subsequently, it was seen that creases were formed and the thin film was buckled after 60 seconds, and, at the same time, it was observed that bending of the thin film in the axial direction was induced. Accordingly, a tubular microelectrode in a state in which its length in the major axis direction was maintained was obtained. The time from when the EDTA solution is added to when a tubular microelectrode is completed can be controlled with the final concentration of the EDTA solution that is added and the type of solution in which the substrate is immersed. In this example, when a calcium alginate gel layer of the sacrificial layer 13 with a length of 200 μm, a width of 400 μm, and a thickness of 40 nm was immersed in 200 μL of pure water, and 5 μL of 0.5M EDTA solution was added thereto, the removal was possible within approximately 20 seconds. Meanwhile, the layered member 20 was buckled approximately 60 seconds after the EDTA solution was added, regardless of the concentration of the EDTA solution.

Figure 4:
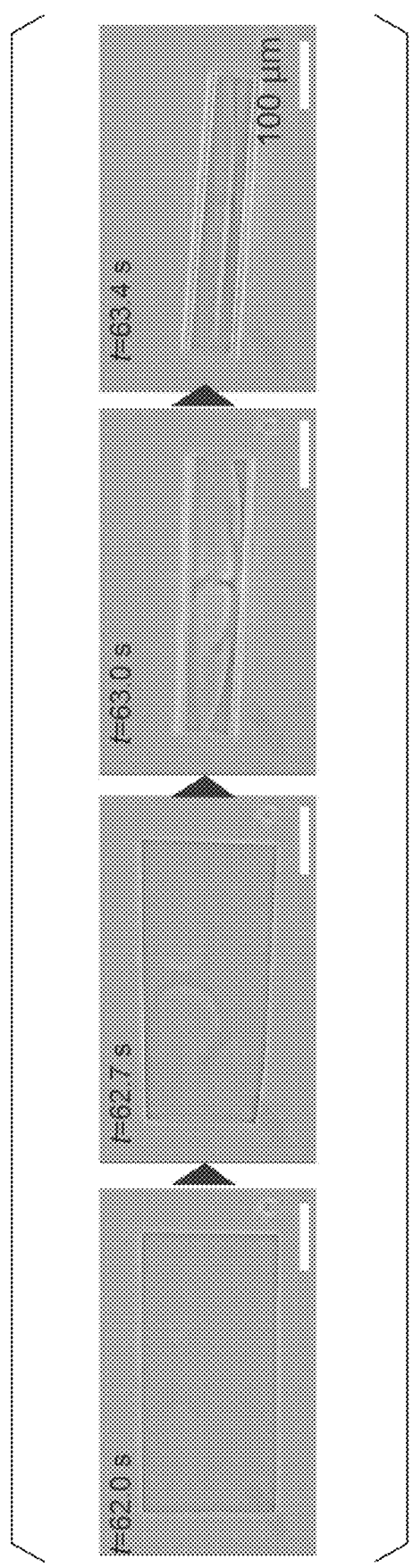
FIG. 4 shows phase-contrast microscope images showing the manner of self-folding from a rectangular layered member to a tubular three-dimensional curved shape after an EDTA solution is added.

FIG. 4 shows the procedure from when the EDTA solution is added to when a tubular microelectrode is completed.

[Example 3] Control of Three-Dimensional Curved Shape

The bending is caused by stress distribution in the thickness direction of the layered member, and thus the curvature of the bending can be controlled by changing the volume of the layered member.

Figure 5:
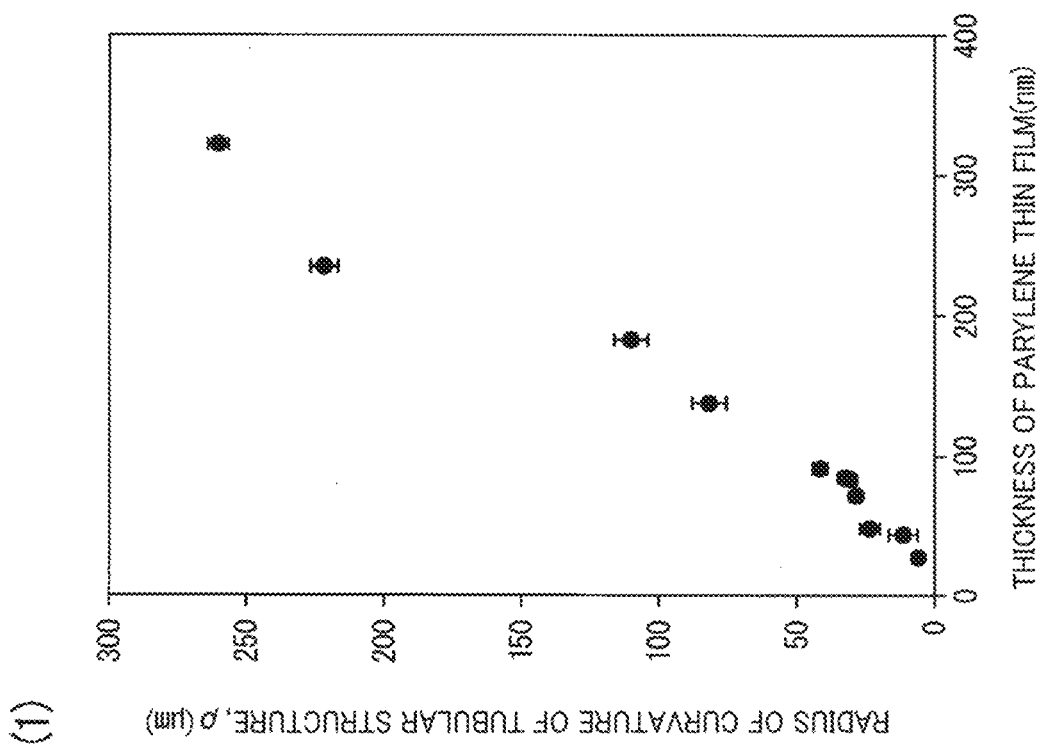
FIG. 5 shows a relation between the radius of curvature of a tubular microelectrode that is an embodiment of the present invention and the thickness of layers of the layered member.

FIG. 5(1) shows a result of evaluation of a correlation between the radius of curvature and the thickness of the parylene layer (the polymer compound layer 12) when a single-layered graphene as the conductive layer 11 was transferred to the parylene layer with a length of 200 μm and a width of 400 μm. It was observed that, when the thickness of the parylene layer (the polymer compound layer 12) increases, the moment of inertia of area of the layered structure increases under constant stress, and bending is unlikely to occur.

On the other hand, it was also seen that, when the thickness of the parylene layer (the polymer compound layer 12) is constant at 84.5 nm, if the number of graphene layers (the conductive layer 11) transferred to the surface of the parylene layer (the polymer compound layer 12) with a length of 200 μm and a width of 400 μm increases, and the final radius of curvature of the tubular microelectrode decreases (FIG. 5(2)). Thus, it was seen that it is possible to produce an electrode with a more minute three-dimensional curved shape, by increasing the thickness of the graphene layer.

Furthermore, after the three-dimensional curved shape is formed, the tubular microelectrode is completely separated from the substrate 10. Accordingly, those practicing the invention can perform handling such as collecting or moving through a pipetting operation, and, furthermore, form a plurality of tubular microelectrodes into an organized structure using a glass capillary.

[Example 4] Optical and Electrical Properties of Tubular Microelectrode

Figure 6:
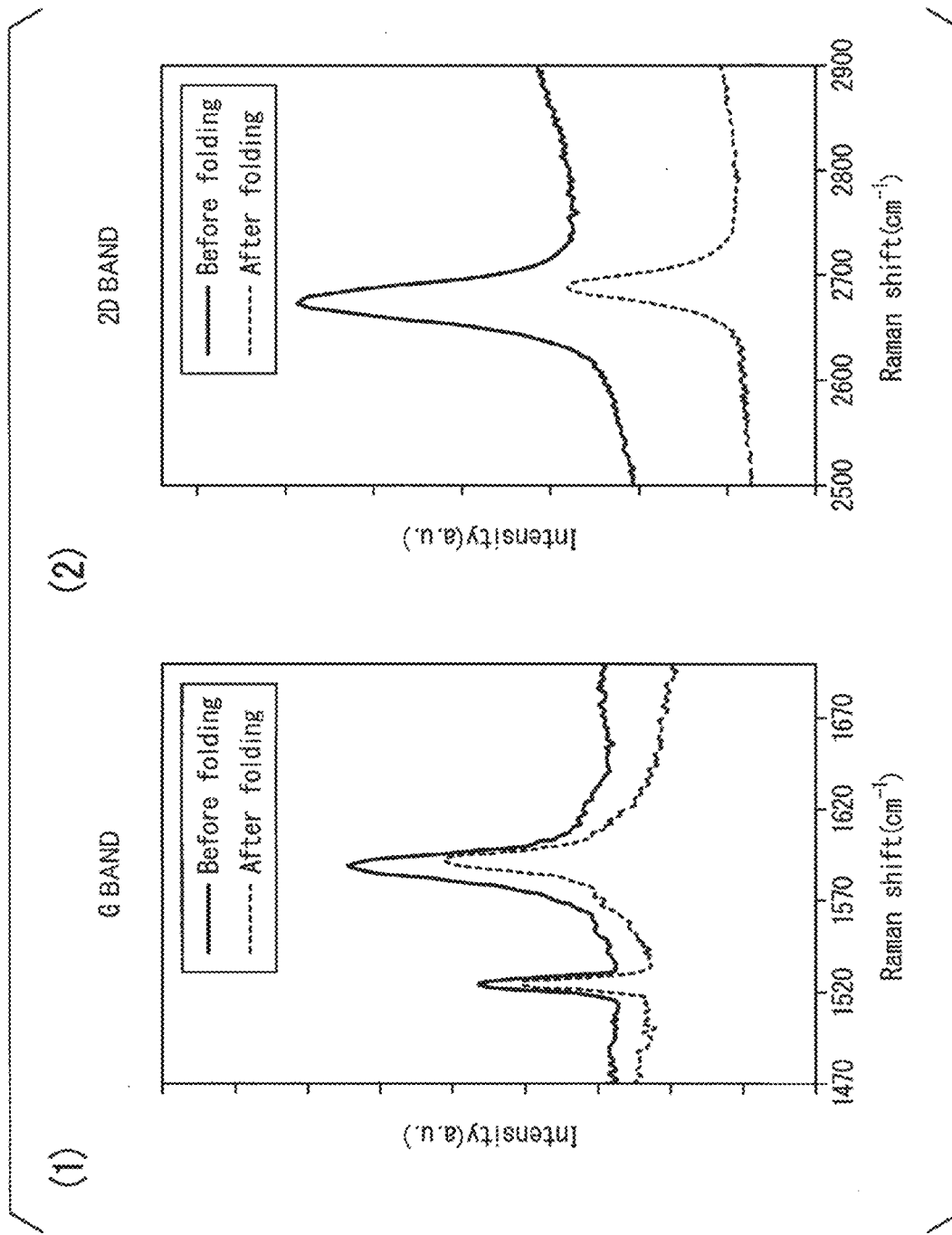
FIG. 6 shows a change between the Raman spectra before and after self-folding of a tubular microelectrode that is an embodiment of the present invention. The Raman spectra of the G band (1) and the 2D band (2) of a graphene layer in the shape of a two-dimensional plane are shown as "Before folding". The Raman spectra of the G band (1) and the 2D band (2) of a three-dimensional microelectrode including two layers constituted by the parylene layer and the graphene layer are shown as "After folding".

The optical properties of the produced tubular microelectrode were evaluated. FIGS. 6(1) and 6(2) show the results of spectra measured using a Raman microscope. In the graphene layer (the conductive layer 11) before folding into a three-dimensional curved shape, both the G band and the 2D band showed spectra similar to those of ordinary CVD graphene (Before folding in FIGS. 6(1) and 6(2)). On the other hand, in the three-dimensional microelectrode including two layers constituted by the parylene layer and the graphene layer, the G band showed shift of the peak position toward the long-wavelength side resulting from the three-dimensional tubular shape (After folding on FIG. 6(1)). Also, the 2D band showed shift of the peak position toward the long-wavelength side (After folding in FIG. 6(2)).

Figure 7:
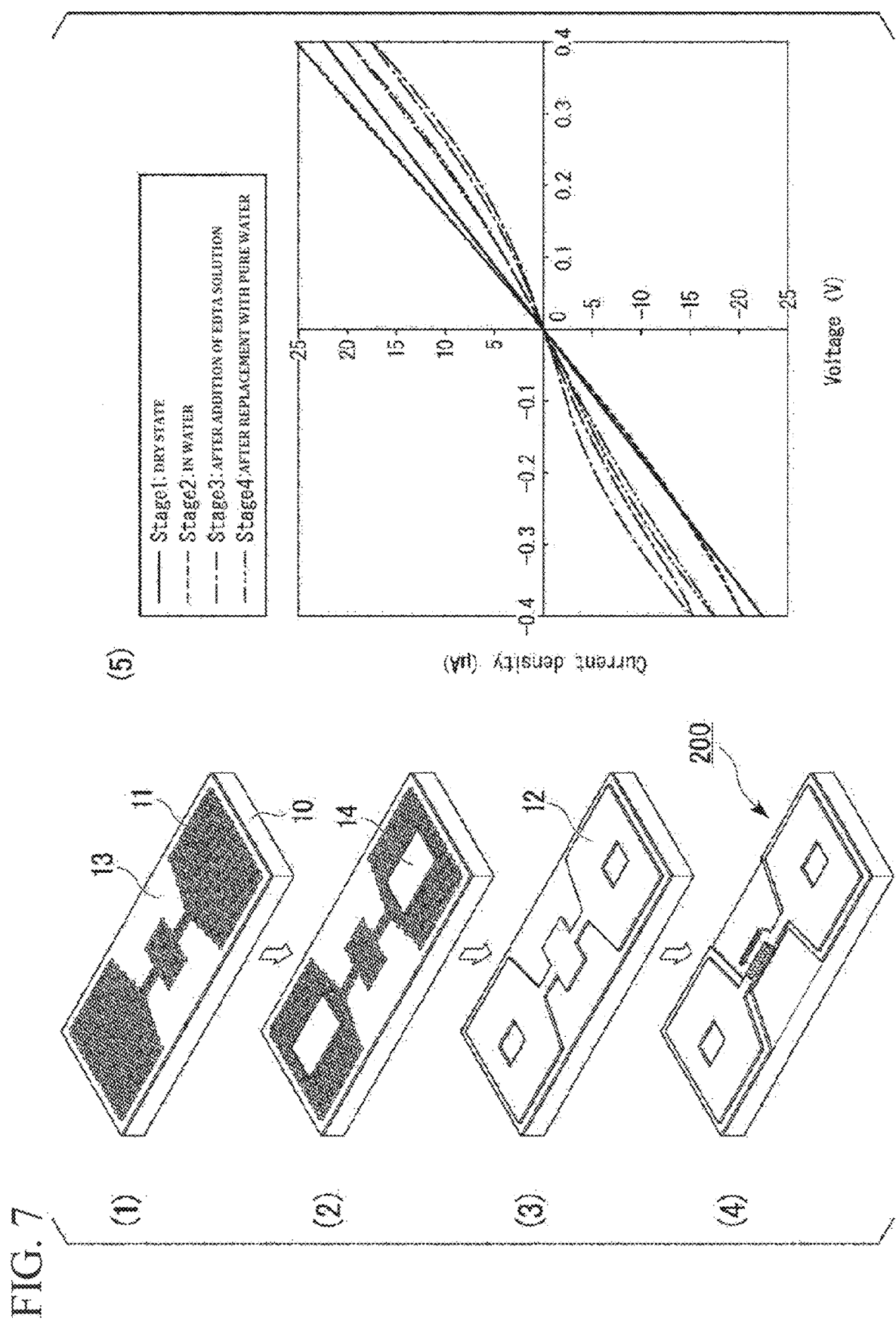
FIG. 7 shows a change between the electrical properties before and after self-folding of a tubular microelectrode that is an embodiment of the present invention.

[Example 5] Change Between the Electrical Properties Before and after Self-Folding A microelectrode with a three-dimensional curved shape was produced according to the process shown in FIGS. 7(1) to 7(4).

A sacrificial layer 13 was formed on a substrate 10, and a conductive layer 11 was transferred to the surface thereof (FIG. 7(1)). The substrate 10, the sacrificial layer 13, and the conductive layer 11 were as in Example 1. Next, a gold electrode (a metal layer 14) was vapor-deposited to each of the two ends of the conductive layer 11 (FIG. 7(2)). Subsequently, a parylene layer (the polymer compound layer 12) was vapor-deposited, and the surface thereof was subjected to patterning (FIG. 7(3)). Then, an EDTA solution was added, and thus a microelectrode 200 whose structure was changed into a recessed shape was obtained (FIG. 7(4)).

FIG. 7(5) shows I-V curves of the microelectrode 200 before and after self-folding described above.

It was seen from the result shown in FIG. 7(1) that a change in the resistance caused by a change in the structure was observed, but breakage did not occur even when the three-dimensional curved shape was formed, and stable conductivity was maintained.

[Example 6] Production of Microelectrodes with Various Three-Dimensional Shapes

The radius of curvature of a tubular microelectrode is defined by the thicknesses of the conductive layer and the polymer compound layer (FIG. 5), and it is possible to form various three-dimensional curved shapes other than a tubular shape while maintaining a constant radius of curvature, by changing the two-dimensional pattern.

If the two-dimensional shape of the layered member was set to a radial pattern, a spherical gripper structure was obtained (FIG. 8(1)). The curvature of the curve of each leg at that time was defined by the thickness of the conductive layer (e.g., the number of graphene layers) and the thickness of the polymer compound layer as in the case of a tubular shape. Also, if a two-dimensional pattern in which hexagons are arranged adjacent to each other to form an array was formed, a tubular microelectrode that was larger, hollow, and had higher material permeability was produced (FIG. 8(2)). If a two-dimensional pattern structure of parallelograms in which two sides of each rectangle are inclined was formed, a coil-like structure wound along the inclined sides was obtained (FIG. 8(3)). This coil structure can be applied as an electrode element whose structure can be flexibly changed in the major axis direction, and that is unlikely to break and is elastic.

[Example 7] Control of Bending Direction with Crystal Orientation of Graphene

Graphene in a millimeter size was produced from single crystal (FIG. 9(1)), and transferred to a thin parylene film. As a result, it was seen that bending occurred in the armchair direction of the graphene single crystal, and the zigzag direction matched the major axis direction of the tubular microelectrode (FIG. 9(2)). This indicates that portions in which points of carbon atoms facing each other in aromatic rings of graphene are located adjacent to each other occupy a larger area than portions in which sides of carbon atoms facing each other are located close to each other (FIG. 9(3)). It was seen from this result that the crystal orientation of graphene can define the bending direction in a phenomenon of macro three-dimensional folding.

INDUSTRIAL APPLICABILITY

According to the present invention, it is possible to fold a microelectrode into a three-dimensional curved shape, while changing the optical properties and electrical properties in a shape specific manner, and preventing breakage and maintaining conductivity.

The microelectrode of the present invention and the integrated device including the microelectrode in an integrated manner can be applied as device elements that are implanted on a living body and extracellular potential measuring elements.

REFERENCE SIGNS LIST

10 Substrate
11 Conductive layer
12 Polymer compound layer
13 Sacrificial layer
14 Metal layer
15 Resist layer
20 Layered member
100, 200 Microelectrode

The invention claimed is:
1. A method of producing a microelectrode with a three-dimensional curved shape, the method comprising steps of:
(a) forming a layered member comprising:
a polymer compound layer which is a layer comprising a polymer compound having an aromatic ring, wherein a thickness of the polymer compound layer is 10 to 900 nm, and
a conductive layer which is a layer comprising a conductive material, wherein a thickness of the conductive layer is 0.3 to 10 nm; and
(b) allowing the layered member to form a three-dimensional curved shape in a self-organized manner, using a strain gradient in a thickness direction of the layered member as a driving force.
2. The method of producing a microelectrode with a three-dimensional curved shape according to claim 1, further comprising a step of:
(c) patterning a part or all of the layers of the layered member into any shape, after the step (a) and before the step (b).

* * * * *